US011410778B2

(12) United States Patent
Ravindranathan et al.

(10) Patent No.: US 11,410,778 B2
(45) Date of Patent: Aug. 9, 2022

(54) MACHINE LEARNING FOR AUTOMATICALLY PROVIDING NOTIFICATIONS AND PROVIDING CONTENT DYNAMICALLY

(71) Applicant: Optum, Inc., Minnetonka, MN (US)

(72) Inventors: Rama S. Ravindranathan, Basking Ridge, NJ (US); Guerino Bonetti, Basking Ridge, NJ (US); Ravi M. Shanbhag, Minnetonka, MN (US)

(73) Assignee: Optum, Inc., Minnetonka, MN (US)

( * ) Notice: Subject to any disclaimer, the term of this patent is extended or adjusted under 35 U.S.C. 154(b) by 127 days.

(21) Appl. No.: 16/274,763

(22) Filed: Feb. 13, 2019

(65) Prior Publication Data

US 2020/0258634 A1 Aug. 13, 2020

(51) Int. Cl.
*G16H 50/30* (2018.01)
*G06K 9/62* (2022.01)
*G06N 20/20* (2019.01)

(52) U.S. Cl.
CPC .......... *G16H 50/30* (2018.01); *G06K 9/6257* (2013.01); *G06N 20/20* (2019.01)

(58) Field of Classification Search
CPC ... G06Q 10/0635; H04L 67/22; H04L 67/306; G16H 10/60; G16H 50/70; G16H 50/20; G16H 50/30; G16H 20/60; G06N 20/20; G06K 9/6257
USPC ...................................................... 705/3, 2
See application file for complete search history.

(56) References Cited

U.S. PATENT DOCUMENTS

| 9,536,052 | B2 | 1/2017 | Amarasingham et al. |
| 9,852,266 | B2 | 12/2017 | Damani et al. |
| 10,741,285 | B2* | 8/2020 | Moturu ................. G16H 40/63 |
| 2009/0275002 | A1 | 11/2009 | Hoggle |
| 2017/0147775 | A1* | 5/2017 | Ohnemus ............... G16H 10/20 |
| 2020/0251213 | A1* | 8/2020 | Tran ....................... G06N 20/00 |

FOREIGN PATENT DOCUMENTS

WO 1996/039050 A2 12/1996

OTHER PUBLICATIONS

Planas et al., "Guidelines For Colorectal Cancer: Effects On Nutritional Intervention," Elsevier Ltd. and European Sociate For Clinical Nutrition and Metabolism, (2007), pp. 691-697. DOI: 10.1016/J.CLNU.2007.08.009.
Kulkarni, "Comparison of Image Recognition APIs On Food Images," Dec. 28, 2017 [online], [retrieved from the Internet Jun. 3, 2019], <URL: https://bytes.grubhub.com/https-medium-com-rohan-kulkarni-comparison-of-image-recognition-apis-on-food-images-cddc9105fc33?gi=cb901061ba10> (8 pages).

(Continued)

*Primary Examiner* — John P Go
*Assistant Examiner* — Christopher B Wehrly
(74) *Attorney, Agent, or Firm* — Alston & Bird LLP

(57) ABSTRACT

Methods, apparatus, systems, computing devices, computing entities, and/or the like for using machine learning to predict micropopulation risk scores and use the micropopulation risk scores to predict a composite risk score. The composite risk score and it associated attributes can be used to provide notifications/messages and provide dynamic content to a mobile app.

12 Claims, 13 Drawing Sheets

(56) References Cited

OTHER PUBLICATIONS

Kiss, "Nutrition Support and Dietary Interventions For Patients With Lung Cancer: Current Insights," Lung Cancer: Targets and Therapy, , Auckland, New Zealand, vol. 7, Jan. 27, 2019, pp. 1-9 pages. DOI: 10.2147/LCTT.S85347.
Goates et al., "Economic Burden of Disease-Associated Malnutirition At The State Level," PLoS One, Sep. 21, 2016, pp. 1-15. DOI: 10.1371/journal.pone.0161833.
Clarifai, "What Food Is This? Food Recognition Technology Can Tell You!," [online], [retrieved from the Internet Jun. 3, 2019], <URL: https://blog.clarifai.com/what-food-is-this-food-recognition-technology-can-tell-you>, pp. 1-3.
"You Love Food, Find Out Which Foods Love You Back," Nutrino, [online], [retrieved from the Internet Oct. 25, 2018], <URL: https://www.nutrinohealth.com/>, (8 pages).
"The Possiblity of Food," EatRx, [online], [retrieved from the Internet Jun. 4, 2019], <URL: https://eatrx.com/the-product/>, pp. 1-7.
"Nutrition Therapy to Manage Side Effects," Cancer Treatment Centers of America, [online], [retrieved from the Internet Jun. 3, 2019], <URL: https://www.cancercenter.com/integrative-care/nutrition-therapy>, (2 pages).
"New Data Show U.S. Hospital Readmissions Are 54 Percent Higher For Malnourished Patients," [online], [retrieved from the Internet Jun. 3, 2019], <URL: https://www.nutritioncare.org/Press_Room/2017/New_Data_Show_U_S__Hospital_Readmissions_are_54_Percent__Higher_for_Malnourished_Patients/> (2 pages).
"Foodlg: Food Nutrition Tracker & Planner," YouTube, [online], [retrieved from the Internet Jun. 4, 2019] <URL: https://www.youtube.com/watch?v=8Qi7_gbJLys>, (18 pages).
"Employee Nutrition With Zipongo Supercharges Wellness Programs," [online], [retrieved from the Internet Jun. 4, 2019], <URL: https://meetzipongo.com/zipongo-for-wellness/#corporate_wellness> (11 pages).
"Calorie Mama AI—Food Image Recognition and Calorie Counter Using Deep Learning," [online], [retrieved from the Internet Jun. 4, 2019], <URL: http://www.caloriemama.ai/> (1 page).

\* cited by examiner

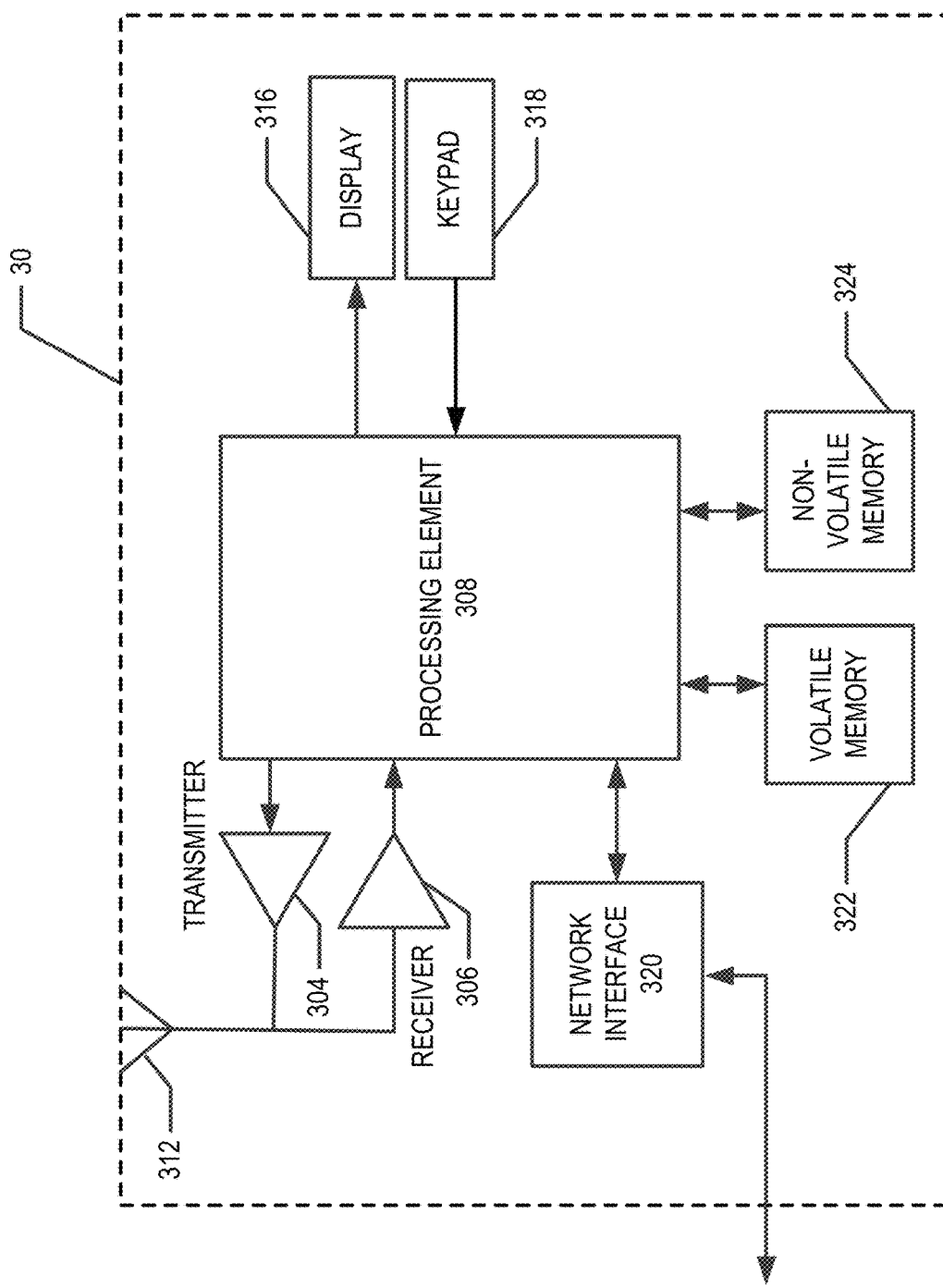

FIG. 5A

| Mem_ID | Mem_Age | Mem_Gender | Mem_Loc | Mem_Prof |
|---|---|---|---|---|
| 1111111 | 29 | M | Southeast | Legal |

FIG. 5B

| Diag_Code | Bill_Code | Service_Date |
|---|---|---|
| S82.92XA | 73590, 99213 | 12.30.2018 |

FIG. 5C

| Prov_Loc | Prov_Spec | Prov_Contract |
|---|---|---|
| West | 20 | Y |

FIG. 6

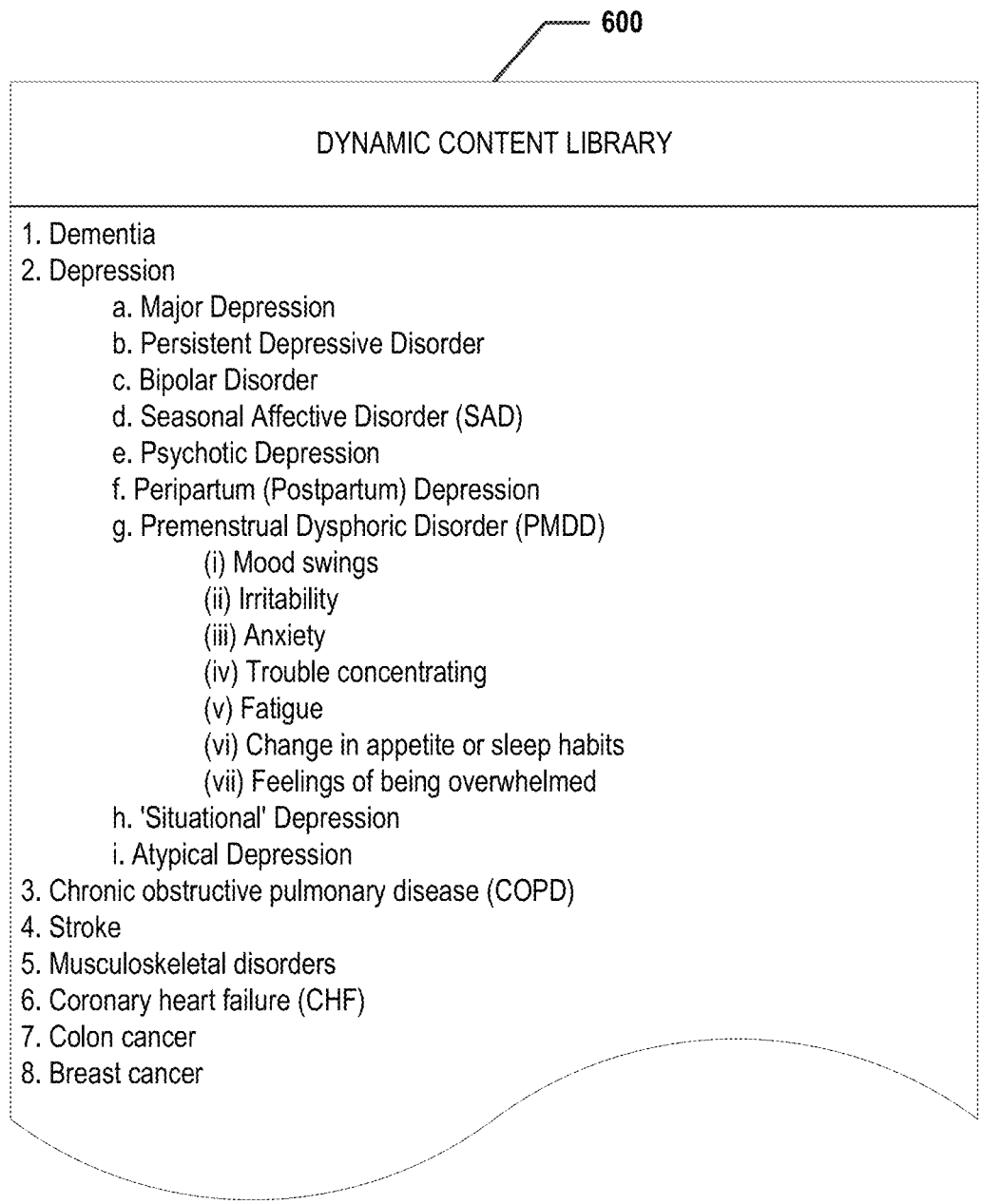

DYNAMIC CONTENT LIBRARY

1. Dementia
2. Depression
    a. Major Depression
    b. Persistent Depressive Disorder
    c. Bipolar Disorder
    d. Seasonal Affective Disorder (SAD)
    e. Psychotic Depression
    f. Peripartum (Postpartum) Depression
    g. Premenstrual Dysphoric Disorder (PMDD)
        (i) Mood swings
        (ii) Irritability
        (iii) Anxiety
        (iv) Trouble concentrating
        (v) Fatigue
        (vi) Change in appetite or sleep habits
        (vii) Feelings of being overwhelmed
    h. 'Situational' Depression
    i. Atypical Depression
3. Chronic obstructive pulmonary disease (COPD)
4. Stroke
5. Musculoskeletal disorders
6. Coronary heart failure (CHF)
7. Colon cancer
8. Breast cancer

MACHINE LEARNING FOR AUTOMATICALLY PROVIDING NOTIFICATIONS AND PROVIDING CONTENT DYNAMICALLY

BACKGROUND

As will be recognized, patients with chronic conditions are often under diagnosed for malnourishment (under nourished, over nourished, and not having proper nutrients in their system to fight the condition). In many situations, the diagnosis of malnourishment is often ignored and patients fall into a vicious cycle worsening their recovery. The cost of disease-related malnutrition is a significant concern presenting both health risks and increases in health costs. For example, malnourished patients are 54% more likely to be readmitted into a hospital than those that receive nutrition support. Moreover, the prevalence of malnourishment is at its peak due to limitations in personalized solutions (especially for patients with specific cultural, religious, and personal preferences). Further exacerbating the concern, medications and treatment procedures of certain chronic diseases may curb the appetites of patients.

Because diet and nutrition plays an important role in chronic disease management and one's overall health, personalized intervention is an important aspect for curbing disease-related malnourishment. And while solutions like fitness apps, fitness trackers, and/or the like allow consumers to track their dietary intake, plan menus, they do not offer dynamic personalization that's applicable for a patient's clinical condition. Through applied effort, ingenuity, and innovation, the inventors have developed methods, apparatus, systems, computing devices, computing entities, and/or for overcoming these challenges—embodiments of which are detail herein.

BRIEF SUMMARY

In general, embodiments of the present invention provide methods, apparatus, systems, computing devices, computing entities, and/or the like.

In accordance with one aspect, a method is provided. In one embodiment, the method comprises predicting, using one or more first machine learning models, a first micropopulation risk score for a user, wherein the first micropopulation risk score corresponds to a first micropopulation; predicting, using one or more second machine learning models, a second micropopulation risk score for the user, wherein the second micropopulation risk score corresponds to a second micropopulation; predicting, using one or more composite second machine learning models and based at least in part on the first micropopulation risk score and the second micropopulation risk score, a composite risk score for the user; determining whether the composite risk score for the user satisfies a configurable risk score threshold; and responsive to determining that the composite risk score for the user satisfies the configurable risk score threshold, automatically providing a notification to the user based at least in part on the user's notifications preferences stored in a user profile.

In accordance with another aspect, a computer program product is provided. The computer program product may comprise at least one computer-readable storage medium having computer-readable program code portions stored therein, the computer-readable program code portions comprising executable portions configured to predict, using one or more first machine learning models, a first micropopulation risk score for a user, wherein the first micropopulation risk score corresponds to a first micropopulation; predict, using one or more second machine learning models, a second micropopulation risk score for the user, wherein the second micropopulation risk score corresponds to a second micropopulation; predict, using one or more composite second machine learning models and based at least in part on the first micropopulation risk score and the second micropopulation risk score, a composite risk score for the user; determine whether the composite risk score for the user satisfies a configurable risk score threshold; and responsive to determining that the composite risk score for the user satisfies the configurable risk score threshold, automatically provide a notification to the user based at least in part on the user's notifications preferences stored in a user profile.

In accordance with yet another aspect, a computing system comprising at least one processor and at least one memory including computer program code is provided. In one embodiment, the at least one memory and the computer program code may be configured to, with the processor, cause the apparatus to predict, using one or more first machine learning models, a first micropopulation risk score for a user, wherein the first micropopulation risk score corresponds to a first micropopulation; predict, using one or more second machine learning models, a second micropopulation risk score for the user, wherein the second micropopulation risk score corresponds to a second micropopulation; predict, using one or more composite second machine learning models and based at least in part on the first micropopulation risk score and the second micropopulation risk score, a composite risk score for the user; determine whether the composite risk score for the user satisfies a configurable risk score threshold; and responsive to determining that the composite risk score for the user satisfies the configurable risk score threshold, automatically provide a notification to the user based at least in part on the user's notifications preferences stored in a user profile.

BRIEF DESCRIPTION OF THE SEVERAL VIEWS OF THE DRAWING(S)

Having thus described the invention in general terms, reference will now be made to the accompanying drawings, which are not necessarily drawn to scale, and wherein:

FIG. 3 is a schematic of a user computing entity in accordance with certain embodiments of the present invention;

FIGS. 5A, 5B, and 5C illustrate exemplary features for ingestion by one or more machine learning models in accordance with certain embodiments of the present invention;

FIG. 6 illustrates an exemplary dynamic content library in accordance with certain embodiments of the present invention;

Figure 1:
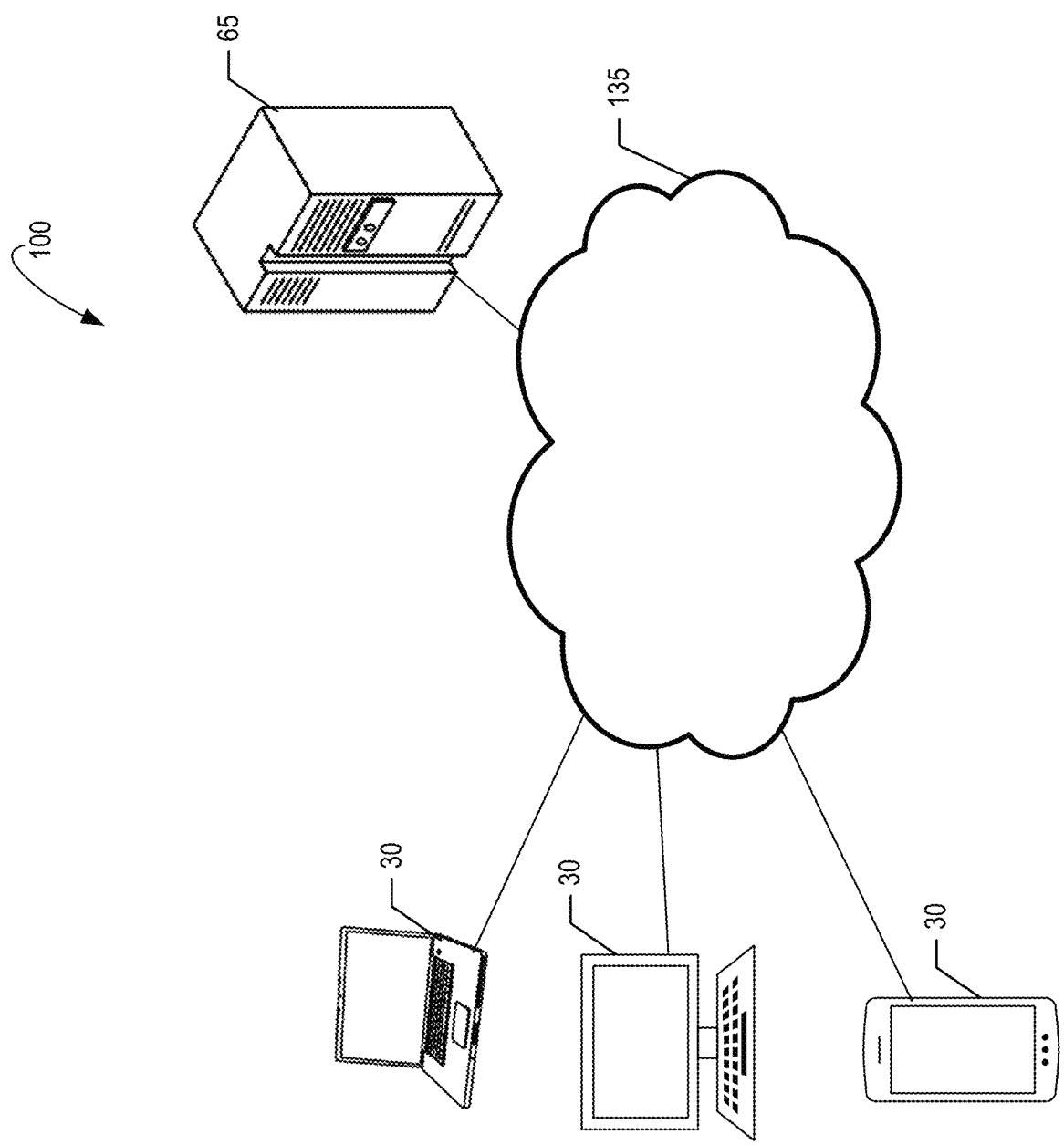
FIG. 1 is a diagram of a data analytic system that can be used in conjunction with various embodiments of the present invention.

FIGS. 7-10 provide exemplary interfaces that can be dynamically updated in accordance with embodiments of the present invention.

DETAILED DESCRIPTION OF SOME EXAMPLE EMBODIMENTS

Various embodiments of the present invention now will be described more fully hereinafter with reference to the accompanying drawings, in which some, but not all embodiments of the inventions are shown. Indeed, these inventions may be embodied in many different forms and should not be construed as limited to the embodiments set forth herein; rather, these embodiments are provided so that this disclosure will satisfy applicable legal requirements. The term "or" (also designated as "/") is used herein in both the alternative and conjunctive sense, unless otherwise indicated. The terms "illustrative" and "exemplary" are used to be examples with no indication of quality level. Like numbers refer to like elements throughout.

I. Computer Program Products, Methods, and Computing Entities

Embodiments of the present invention may be implemented in various ways, including as computer program products that comprise articles of manufacture. Such computer program products may include one or more software components including, for example, software objects, methods, data structures, and/or the like. A software component may be coded in any of a variety of programming languages. An illustrative programming language may be a lower-level programming language such as an assembly language associated with a particular hardware architecture and/or operating system platform. A software component comprising assembly language instructions may require conversion into executable machine code by an assembler prior to execution by the hardware architecture and/or platform. Another example programming language may be a higher-level programming language that may be portable across multiple architectures. A software component comprising higher-level programming language instructions may require conversion to an intermediate representation by an interpreter or a compiler prior to execution.

Other examples of programming languages include, but are not limited to, a macro language, a shell or command language, a job control language, a script language, a database query or search language, and/or a report writing language. In one or more example embodiments, a software component comprising instructions in one of the foregoing examples of programming languages may be executed directly by an operating system or other software component without having to be first transformed into another form. A software component may be stored as a file or other data storage construct. Software components of a similar type or functionally related may be stored together such as, for example, in a particular directory, folder, or library. Software components may be static (e.g., pre-established or fixed) or dynamic (e.g., created or modified at the time of execution).

A computer program product may include a non-transitory computer-readable storage medium storing applications, programs, program modules, scripts, source code, program code, object code, byte code, compiled code, interpreted code, machine code, executable instructions, and/or the like (also referred to herein as executable instructions, instructions for execution, computer program products, program code, and/or similar terms used herein interchangeably). Such non-transitory computer-readable storage media include all computer-readable media (including volatile and non-volatile media).

In one embodiment, a non-volatile computer-readable storage medium may include a floppy disk, flexible disk, hard disk, solid-state storage (SSS) (e.g., a solid state drive (SSD), solid state card (SSC), solid state module (SSM), enterprise flash drive, magnetic tape, or any other non-transitory magnetic medium, and/or the like. A non-volatile computer-readable storage medium may also include a punch card, paper tape, optical mark sheet (or any other physical medium with patterns of holes or other optically recognizable indicia), compact disc read only memory (CD-ROM), compact disc-rewritable (CD-RW), digital versatile disc (DVD), Blu-ray disc (BD), any other non-transitory optical medium, and/or the like. Such a non-volatile computer-readable storage medium may also include read-only memory (ROM), programmable read-only memory (PROM), erasable programmable read-only memory (EPROM), electrically erasable programmable read-only memory (EEPROM), flash memory (e.g., Serial, NAND, NOR, and/or the like), multimedia memory cards (MMC), secure digital (SD) memory cards, SmartMedia cards, CompactFlash (CF) cards, Memory Sticks, and/or the like. Further, a non-volatile computer-readable storage medium may also include conductive-bridging random access memory (CBRAM), phase-change random access memory (PRAM), ferroelectric random-access memory (FeRAM), non-volatile random-access memory (NVRAM), magnetoresistive random-access memory (MRAM), resistive random-access memory (RRAM), Silicon-Oxide-Nitride-Oxide-Silicon memory (SONOS), floating junction gate random access memory (FJG RAM), Millipede memory, racetrack memory, and/or the like.

In one embodiment, a volatile computer-readable storage medium may include random access memory (RAM), dynamic random access memory (DRAM), static random access memory (SRAM), fast page mode dynamic random access memory (FPM DRAM), extended data-out dynamic random access memory (EDO DRAM), synchronous dynamic random access memory (SDRAM), double data rate synchronous dynamic random access memory (DDR SDRAM), double data rate type two synchronous dynamic random access memory (DDR2 SDRAM), double data rate type three synchronous dynamic random access memory (DDR3 SDRAM), Rambus dynamic random access memory (RDRAM), Twin Transistor RAM (TTRAM), Thyristor RAM (T-RAM), Zero-capacitor (Z-RAM), Rambus in-line memory module (RIMM), dual in-line memory module (DIMM), single in-line memory module (SIMM), video random access memory (VRAM), cache memory (including various levels), flash memory, register memory, and/or the like. It will be appreciated that where embodiments are described to use a computer-readable storage medium, other types of computer-readable storage media may be substituted for or used in addition to the computer-readable storage media described above.

As should be appreciated, various embodiments of the present invention may also be implemented as methods, apparatus, systems, computing devices, computing entities, and/or the like. As such, embodiments of the present invention may take the form of a data structure, apparatus, system, computing device, computing entity, and/or the like executing instructions stored on a computer-readable storage medium to perform certain steps or operations. Thus, embodiments of the present invention may also take the form of an entirely hardware embodiment, an entirely computer program product embodiment, and/or an embodiment that comprises combination of computer program products and hardware performing certain steps or operations.

Embodiments of the present invention are described below with reference to block diagrams and flowchart illustrations. Thus, it should be understood that each block of the block diagrams and flowchart illustrations may be implemented in the form of a computer program product, an entirely hardware embodiment, a combination of hardware and computer program products, and/or apparatus, systems, computing devices, computing entities, and/or the like carrying out instructions, operations, steps, and similar words used interchangeably (e.g., the executable instructions, instructions for execution, program code, and/or the like) on a computer-readable storage medium for execution. For example, retrieval, loading, and execution of code may be performed sequentially such that one instruction is retrieved, loaded, and executed at a time. In some exemplary embodiments, retrieval, loading, and/or execution may be performed in parallel such that multiple instructions are retrieved, loaded, and/or executed together. Thus, such embodiments can produce specifically-configured machines performing the steps or operations specified in the block diagrams and flowchart illustrations. Accordingly, the block diagrams and flowchart illustrations support various combinations of embodiments for performing the specified instructions, operations, or steps.

II. Exemplary System Architecture

FIG. 1 provides an illustration of a data analytic system 100 that can be used in conjunction with various embodiments of the present invention. As shown in FIG. 1, the data analytic system 100 may comprise one or more analytic computing entities 65, one or more user computing entities 30, one or more networks 135, and/or the like. Each of the components of the system may be in electronic communication with, for example, one another over the same or different wireless or wired networks 135 including, for example, a wired or wireless Personal Area Network (PAN), Local Area Network (LAN), Metropolitan Area Network (MAN), Wide Area Network (WAN), and/or the like. Additionally, while FIG. 1 illustrate certain system entities as separate, standalone entities, the various embodiments are not limited to this particular architecture.

a. Exemplary Analytic Computing Entity

Figure 2A:
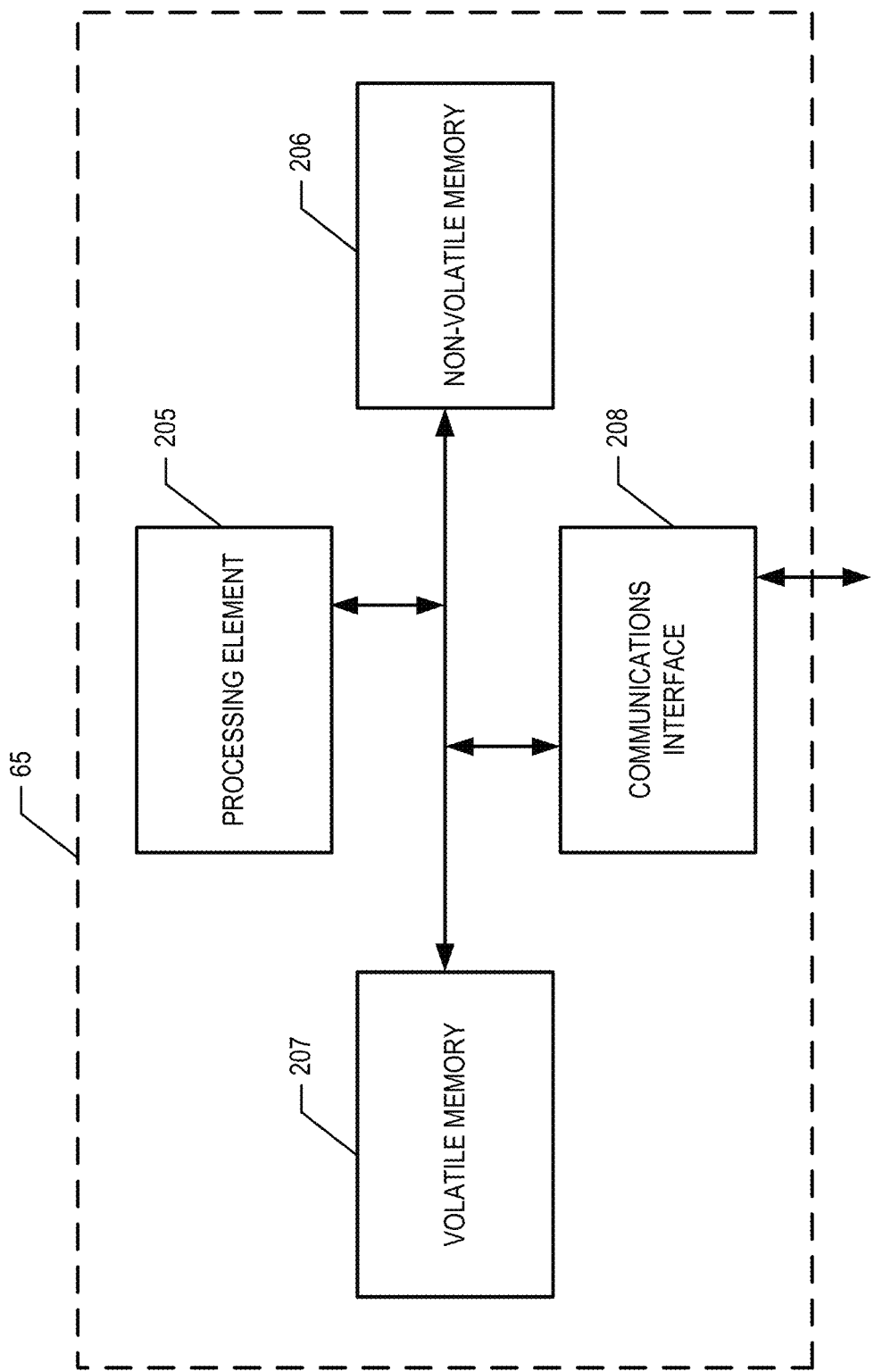
FIG. 2A is a schematic of an analytic computing entity in accordance with certain embodiments of the present invention.
Figure 2B:
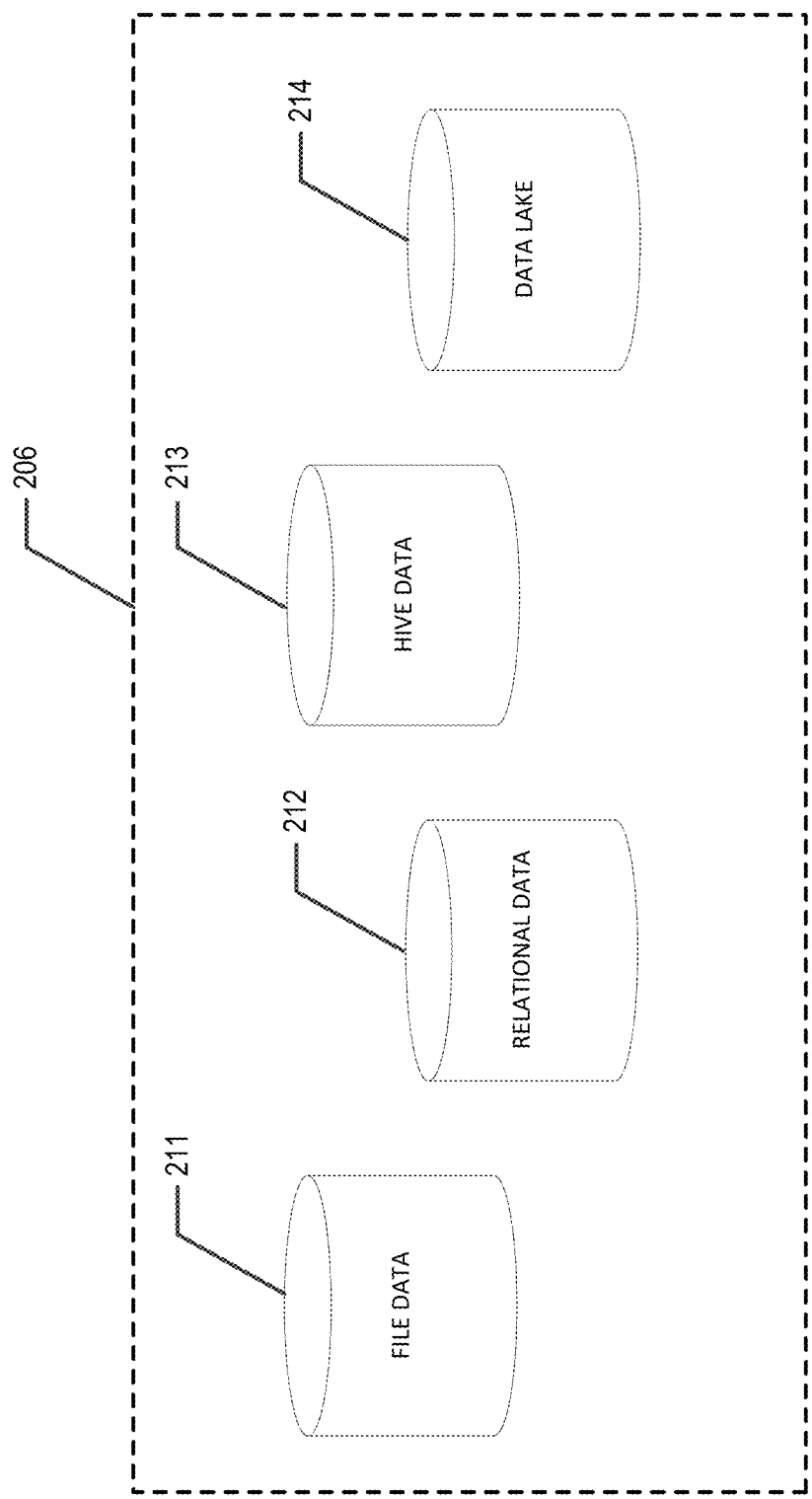
FIG. 2B is a schematic representation of a memory media storing various types of health-related information/data.
Figure 2C:
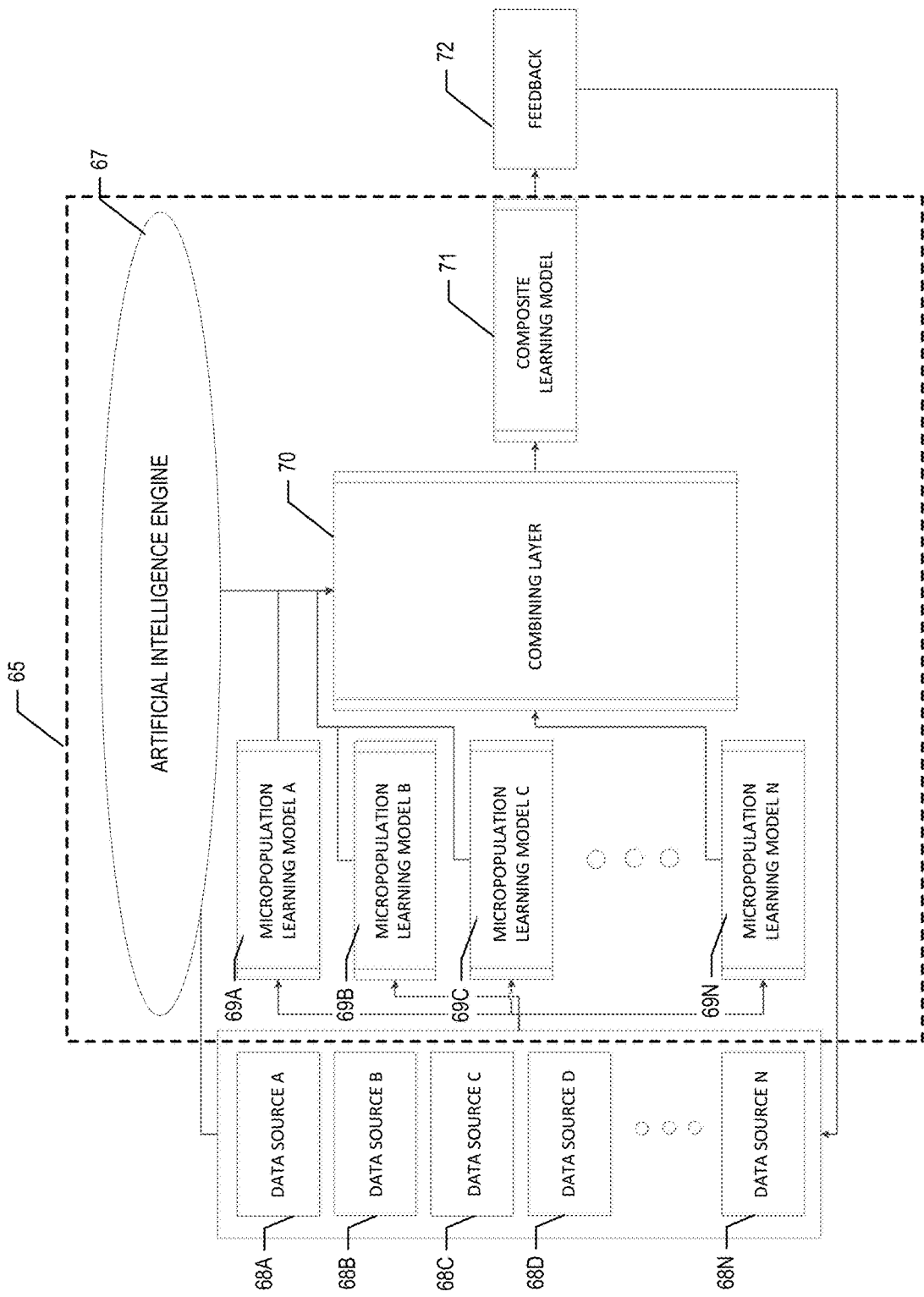
FIG. 2C is a schematic representation of components of an artificial intelligence engine executing on the analytic computing entity interacting with various other components in accordance with certain embodiments of the present invention.

FIG. 2A provides a schematic of an analytic computing entity 65 according to one embodiment of the present invention. In general, the terms computing entity, entity, device, system, and/or similar words used herein interchangeably may refer to, for example, one or more computers, computing entities, desktop computers, mobile phones, tablets, phablets, notebooks, laptops, distributed systems, items/devices, terminals, servers or server networks, blades, gateways, switches, processing devices, processing entities, set-top boxes, relays, routers, network access points, base stations, the like, and/or any combination of devices or entities adapted to perform the functions, operations, and/or processes described herein. Such functions, operations, and/or processes may include, for example, transmitting, receiving, operating on, processing, displaying, storing, determining, creating/generating, monitoring, evaluating, comparing, and/or similar terms used herein interchangeably. In one embodiment, these functions, operations, and/or processes can be performed on data, content, information, and/or similar terms used herein interchangeably.

As indicated, in one embodiment, the analytic computing entity 65 may also include one or more network and/or communications interfaces 208 for communicating with various computing entities, such as by communicating data, content, information, and/or similar terms used herein interchangeably that can be transmitted, received, operated on, processed, displayed, stored, and/or the like. For instance, the analytic computing entity 65 may communicate with other computing entities, one or more user computing entities 30, and/or the like.

As shown in FIG. 2A, in one embodiment, the analytic computing entity 65 may include or be in communication with one or more processing elements 205 (also referred to as processors, processing circuitry, and/or similar terms used herein interchangeably) that communicate with other elements within the analytic computing entity 65 via a bus, for example, or network connection. As will be understood, the processing element 205 may be embodied in a number of different ways. For example, the processing element 205 may be embodied as one or more complex programmable logic devices (CPLDs), microprocessors, multi-core processors, coprocessing entities, application-specific instruction-set processors (ASIPs), and/or controllers. Further, the processing element 205 may be embodied as one or more other processing devices or circuitry. The term circuitry may refer to an entirely hardware embodiment or a combination of hardware and computer program products. Thus, the processing element 205 may be embodied as integrated circuits, application specific integrated circuits (ASICs), field programmable gate arrays (FPGAs), programmable logic arrays (PLAs), hardware accelerators, other circuitry, and/or the like. As will therefore be understood, the processing element 205 may be configured for a particular use or configured to execute instructions stored in volatile or non-volatile media or otherwise accessible to the processing element 205. As such, whether configured by hardware or computer program products, or by a combination thereof, the processing element 205 may be capable of performing steps or operations according to embodiments of the present invention when configured accordingly.

In one embodiment, the analytic computing entity 65 may further include or be in communication with non-volatile media (also referred to as non-volatile storage, memory, memory storage, memory circuitry and/or similar terms used herein interchangeably). In one embodiment, the non-volatile storage or memory may include one or more non-volatile storage or memory media 206 as described above, such as hard disks, ROM, PROM, EPROM, EEPROM, flash memory, MMCs, SD memory cards, Memory Sticks, CBRAM, PRAM, FeRAM, RRAM, SONOS, racetrack memory, and/or the like. As will be recognized, the non-volatile storage or memory media may store databases, metadata repositories database instances, database management system entities, data, applications, programs, program modules, scripts, source code, object code, byte code, compiled code, interpreted code, machine code, executable instructions, and/or the like. The term database, database instance, database management system entity, and/or similar terms used herein interchangeably and in a general sense to refer to a structured or unstructured collection of information/data that is stored in a computer-readable storage medium.

Memory media 206 (e.g., metadata repository) may also be embodied as a data storage device or devices, as a separate database server or servers, or as a combination of data storage devices and separate database servers. Further, in some embodiments, memory media 206 may be embodied as a distributed repository such that some of the stored information/data is stored centrally in a location within the system and other information/data is stored in one or more remote locations. Alternatively, in some embodiments, the distributed repository may be distributed over a plurality of remote storage locations only. An example of the embodiments contemplated herein would include a cloud data storage system maintained by a third party provider and where some or all of the information/data required for the operation of the data analytic system may be stored. As a person of ordinary skill in the art would recognize, the information/data required for the operation of the data analytic system may also be partially stored in the cloud data storage system and partially stored in a locally maintained data storage system.

Memory media 206 (e.g., metadata repository) may include information/data accessed and/or stored by the data analytic system 100 to facilitate the operations of the system. More specifically, memory media 206 may encompass one or more data stores configured to store information/data usable in certain embodiments. The data stores, metadata repositories, and similar words used herein interchangeably may comprise file data stores 211, relational data stores 212, Hive data stores 213, data lake data stores, and/or various other types of data stores. In one embodiment, the data stores may comprise various types of health-related information/data.

In one embodiment, the health-related information/data may comprise provider information/data having identifying information/data indicative of various providers. The term provider is used generally to refer to any person or entity that provides goods, services, and/or the like. Examples of providers include medical doctors, nurse practitioners, physician assistants, nurses, other medical professionals practicing in one or more of a plurality of medical specialties (e.g., psychiatry, pain management, anesthesiology, general surgery, emergency medicine, and/or the like), hospitals, urgent care centers, diagnostic laboratories, surgery centers, and/or the like. The provider information/data may comprise provider identifiers, provider locations, and/or the like.

In one embodiment, the health-related information/data may comprise member information/data. The member information/data may comprise information/data for a member, such as age, gender, poverty rates, known health conditions, home location, profession, access to medical care, medical history, claim history, member identifier (ID), and/or the like.

In one embodiment, the health-related information/data may comprise transaction information/data, such as claim information/data indicative of claims filed on behalf of a provider for services or products. Moreover, the claim information/data may further comprise prescription claim information/data. Prescription claim information/data may be used to extract information/data such as the identity of entities that prescribe certain drugs and the pharmacies that fill such prescriptions.

In one embodiment, the analytic computing entity 65 may further include or be in communication with volatile media (also referred to as volatile storage, memory, memory storage, memory circuitry and/or similar terms used herein interchangeably). In one embodiment, the volatile storage or memory may also include one or more volatile storage or memory media 207 as described above, such as RAM, DRAM, SRAM, FPM DRAM, EDO DRAM, SDRAM, DDR SDRAM, DDR2 SDRAM, DDR3 SDRAM, RDRAM, RIMM, DIMM, SIMM, VRAM, cache memory, register memory, and/or the like. As will be recognized, the volatile storage or memory media may be used to store at least portions of the databases, database instances, database management system entities, data, applications, programs, program modules, scripts, source code, object code, byte code, compiled code, interpreted code, machine code, executable instructions, and/or the like being executed by, for example, the processing element 308. Thus, the databases, database instances, database management system entities, data, applications, programs, program modules, scripts, source code, object code, byte code, compiled code, interpreted code, machine code, executable instructions, and/or the like may be used to control certain aspects of the operation of the analytic computing entity 65 with the assistance of the processing element 205 and operating system.

As indicated, in one embodiment, the analytic computing entity 65 may also include one or more network and/or communications interfaces 208 for communicating with various computing entities, such as by communicating data, content, information, and/or similar terms used herein interchangeably that can be transmitted, received, operated on, processed, displayed, stored, and/or the like. For instance, the analytic computing entity 65 may communicate with computing entities or communication interfaces of other analytic computing entities 65, user computing entities 30, and/or the like. In this regard, the analytic computing entity 65 may comprise an artificial intelligence engine 67. Thus, the artificial intelligence engine 67 (e.g., executing on the analytic computing entity 65) may comprise one or more machine learning models 69A-69N that generate/predict respective micropopulation scores for users, members, patients, and similar words used herein interchangeably. With the respective micropopulation scores, the artificial intelligence engine 67 (e.g., executing on the analytic computing entity 65) may comprise a composite machine learning model 71 that predicts a composite risk score.

As indicated, in one embodiment, the analytic computing entity 65 may also include one or more network and/or communications interfaces 208 for communicating with various computing entities, such as by communicating data, content, information, and/or similar terms used herein interchangeably that can be transmitted, received, operated on, processed, displayed, stored, and/or the like. Such communication may be executed using a wired data transmission protocol, such as fiber distributed data interface (FDDI), digital subscriber line (DSL), Ethernet, asynchronous transfer mode (ATM), frame relay, data over cable service interface specification (DOCSIS), or any other wired transmission protocol. Similarly, the analytic computing entity 65 may be configured to communicate via wireless external communication networks using any of a variety of protocols, such as general packet radio service (GPRS), Universal Mobile Telecommunications System (UMTS), Code Division Multiple Access 2000 (CDMA2000), CDMA2000 1× (1×RTT), Wideband Code Division Multiple Access (WCDMA), Global System for Mobile Communications (GSM), Enhanced Data rates for GSM Evolution (EDGE), Time Division-Synchronous Code Division Multiple Access (TD-SCDMA), Long Term Evolution (LTE), Evolved Universal Terrestrial Radio Access Network (E-UTRAN), Evolution-Data Optimized (EVDO), High Speed Packet Access (HSPA), High-Speed Downlink Packet Access (HSDPA), IEEE 802.11 (Wi-Fi), Wi-Fi Direct, 802.16 (WiMAX), ultra-wideband (UWB), infrared (IR) protocols, near field communication (NFC) protocols, Wibree, Bluetooth protocols, wireless universal serial bus (USB) protocols, and/or any other wireless protocol. The analytic computing entity 65 may use such protocols and standards to communicate using Border Gateway Protocol (BGP), Dynamic Host Configuration Protocol (DHCP), Domain Name System (DNS), File Transfer Protocol (FTP), Hypertext Transfer Protocol (HTTP), HTTP over TLS/SSL/Secure, Internet Message Access Protocol (IMAP), Network Time Protocol (NTP), Simple Mail Transfer Protocol (SMTP), Telnet, Transport Layer Security (TLS), Secure Sockets Layer (SSL), Internet Protocol (IP), Transmission Control Protocol (TCP), User Datagram Protocol (UDP), Datagram Congestion Control Protocol (DCCP), Stream Control Transmission Protocol (SCTP), HyperText Markup Language (HTML), and/or the like.

As will be appreciated, one or more of the analytic computing entity's components may be located remotely from other analytic computing entity 65 components, such as in a distributed system. Furthermore, one or more of the components may be aggregated and additional components performing functions described herein may be included in the analytic computing entity 65. Thus, the analytic computing entity 65 can be adapted to accommodate a variety of needs and circumstances.

b. Exemplary User Computing Entity

FIG. 3 provides an illustrative schematic representative of a user computing entity 30 that can be used in conjunction with embodiments of the present invention. As will be recognized, the user computing entity may be operated by an agent and include components and features similar to those described in conjunction with the analytic computing entity 65. Further, as shown in FIG. 3, the user computing entity may include additional components and features. For example, the user computing entity 30 can include an antenna 312, a transmitter 304 (e.g., radio), a receiver 306 (e.g., radio), and a processing element 308 that provides signals to and receives signals from the transmitter 304 and receiver 306, respectively. The signals provided to and received from the transmitter 304 and the receiver 306, respectively, may include signaling information/data in accordance with an air interface standard of applicable wireless systems to communicate with various entities, such as an analytic computing entity 65, another user computing entity 30, and/or the like. In this regard, the user computing entity 30 may be capable of operating with one or more air interface standards, communication protocols, modulation types, and access types. More particularly, the user computing entity 30 may operate in accordance with any of a number of wireless communication standards and protocols. In a particular embodiment, the user computing entity 30 may operate in accordance with multiple wireless communication standards and protocols, such as GPRS, UMTS, CDMA2000, 1xRTT, WCDMA, TD-SCDMA, LTE, E-UTRAN, EVDO, HSPA, HSDPA, Wi-Fi, WiMAX, UWB, IR protocols, Bluetooth protocols, USB protocols, and/or any other wireless protocol.

Via these communication standards and protocols, the user computing entity 30 can communicate with various other entities using concepts such as Unstructured Supplementary Service data (USSD), Short Message Service (SMS), Multimedia Messaging Service (MIMS), Dual-Tone Multi-Frequency Signaling (DTMF), and/or Subscriber Identity Module Dialer (SIM dialer). The user computing entity 30 can also download changes, add-ons, and updates, for instance, to its firmware, software (e.g., including executable instructions, applications, program modules), and operating system.

According to one embodiment, the user computing entity 30 may include location determining aspects, devices, modules, functionalities, and/or similar words used herein interchangeably. For example, the user computing entity 30 may include outdoor positioning aspects, such as a location module adapted to acquire, for example, latitude, longitude, altitude, geocode, course, direction, heading, speed, UTC, date, and/or various other information/data. In one embodiment, the location module can acquire data, sometimes known as ephemeris data, by identifying the number of satellites in view and the relative positions of those satellites. The satellites may be a variety of different satellites, including LEO satellite systems, DOD satellite systems, the European Union Galileo positioning systems, the Chinese Compass navigation systems, Indian Regional Navigational satellite systems, and/or the like. Alternatively, the location information/data/data may be determined by triangulating the position in connection with a variety of other systems, including cellular towers, Wi-Fi access points, and/or the like. Similarly, the user computing entity 30 may include indoor positioning aspects, such as a location module adapted to acquire, for example, latitude, longitude, altitude, geocode, course, direction, heading, speed, time, date, and/or various other information/data. Some of the indoor aspects may use various position or location technologies including RFID tags, indoor beacons or transmitters, Wi-Fi access points, cellular towers, nearby computing devices (e.g., smartphones, laptops) and/or the like. For instance, such technologies may include iBeacons, Gimbal proximity beacons, BLE transmitters, Near Field Communication (NFC) transmitters, and/or the like. These indoor positioning aspects can be used in a variety of settings to determine the location of someone or something to within inches or centimeters.

The user computing entity 30 may also comprise a user interface 1100 comprising one or more user input/output interfaces (e.g., a display 316 and/or speaker/speaker driver coupled to a processing element 308 and a touch screen, keyboard, mouse, and/or microphone coupled to a processing element 308). For example, the user output interface may be configured to provide an application, browser, user interface, dashboard, webpage, and/or similar words used herein interchangeably executing on and/or accessible via the user computing entity 30 to cause display or audible presentation of information/data and for user interaction therewith via one or more user input interfaces. The user output interface may be updated dynamically from communication with the analytic computing entity 65. The user input interface can comprise any of a number of devices allowing the user computing entity 30 to receive data, such as a keypad 318 (hard or soft), a touch display, voice/speech or motion interfaces, scanners, readers, or other input device. In embodiments including a keypad 318, the keypad 318 can include (or cause display of) the conventional numeric (0-9) and related keys (#, *), and other keys used for operating the user computing entity 30 and may include a full set of alphabetic keys or set of keys that may be activated to provide a full set of alphanumeric keys. In addition to providing input, the user input interface can be used, for example, to activate or deactivate certain functions, such as screen savers and/or sleep modes. Through such inputs the user computing entity 30 can collect information/data, user interaction/input, and/or the like.

The user computing entity 30 can also include volatile storage or memory 322 and/or non-volatile storage or memory 324, which can be embedded and/or may be removable. For example, the non-volatile memory may be ROM, PROM, EPROM, EEPROM, flash memory, MMCs, SD memory cards, Memory Sticks, CBRAM, PRAM, FeRAM, RRAM, SONOS, racetrack memory, and/or the like. The volatile memory may be RAM, DRAM, SRAM, FPM DRAM, EDO DRAM, SDRAM, DDR SDRAM, DDR2 SDRAM, DDR3 SDRAM, RDRAM, RIMM, DIMM, SIMM, VRAM, cache memory, register memory, and/or the like. The volatile and non-volatile storage or memory can store databases, database instances, database management system entities, data, applications, programs, program modules, scripts, source code, object code, byte code, compiled code, interpreted code, machine code, executable instructions, and/or the like to implement the functions of the user computing entity 30.

c. Exemplary Networks

In one embodiment, the networks 135 may include, but are not limited to, any one or a combination of different types of suitable communications networks such as, for example, cable networks, public networks (e.g., the Internet), private networks (e.g., frame-relay networks), wireless networks, cellular networks, telephone networks (e.g., a public switched telephone network), or any other suitable private and/or public networks. Further, the networks 135 may have any suitable communication range associated therewith and may include, for example, global networks (e.g., the Internet), MANs, WANs, LANs, or PANs. In addition, the networks 135 may include any type of medium over which network traffic may be carried including, but not limited to, coaxial cable, twisted-pair wire, optical fiber, a hybrid fiber coaxial (HFC) medium, microwave terrestrial transceivers, radio frequency communication mediums, satellite communication mediums, or any combination thereof, as well as a variety of network devices and computing platforms provided by network providers or other entities.

III. Exemplary System Operation

Figure 4A:
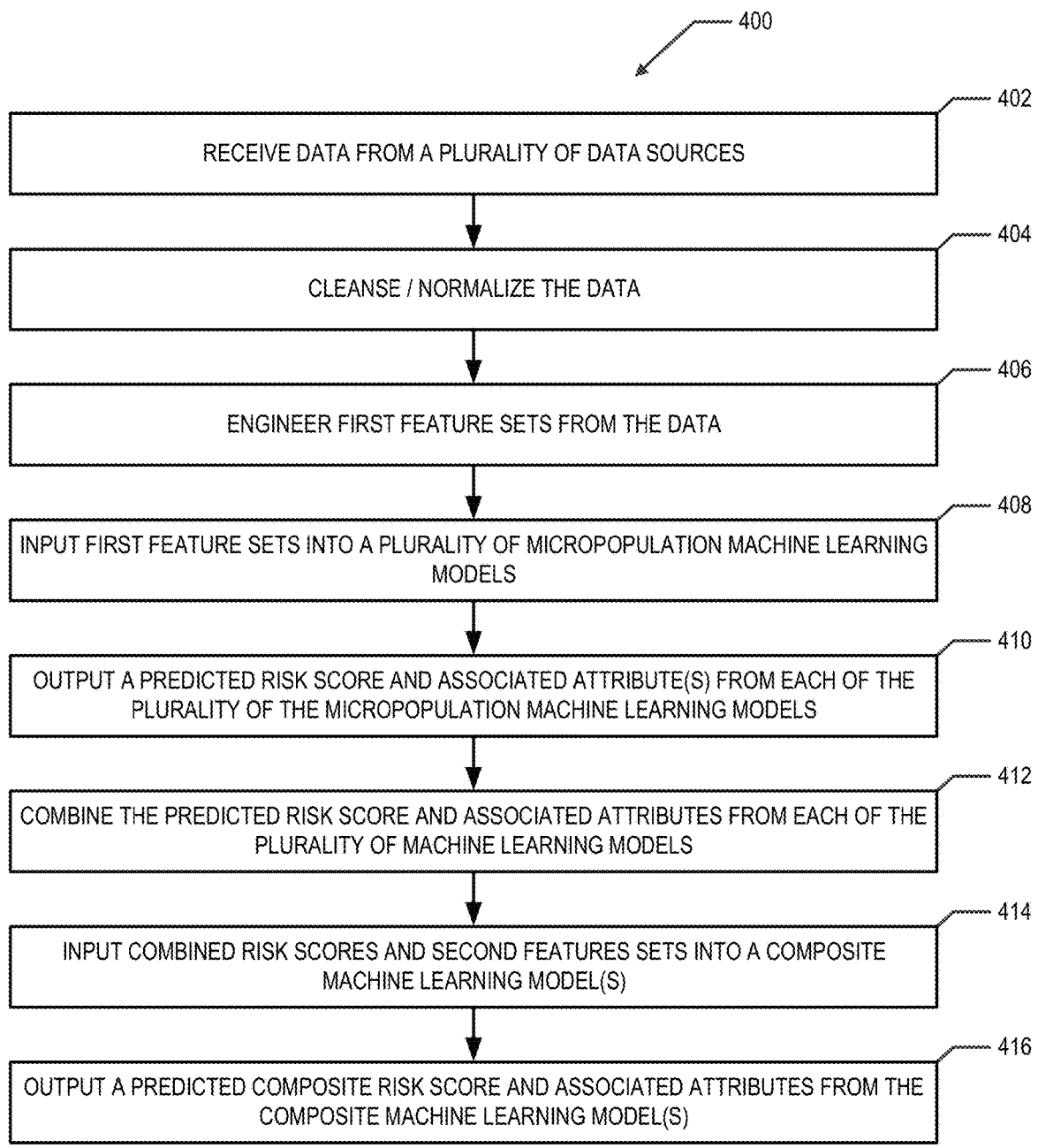
FIGS. 4A and 4B are flowcharts for exemplary connections, operations, steps, and processes in accordance with certain embodiments of the present invention.
Figure 4B:
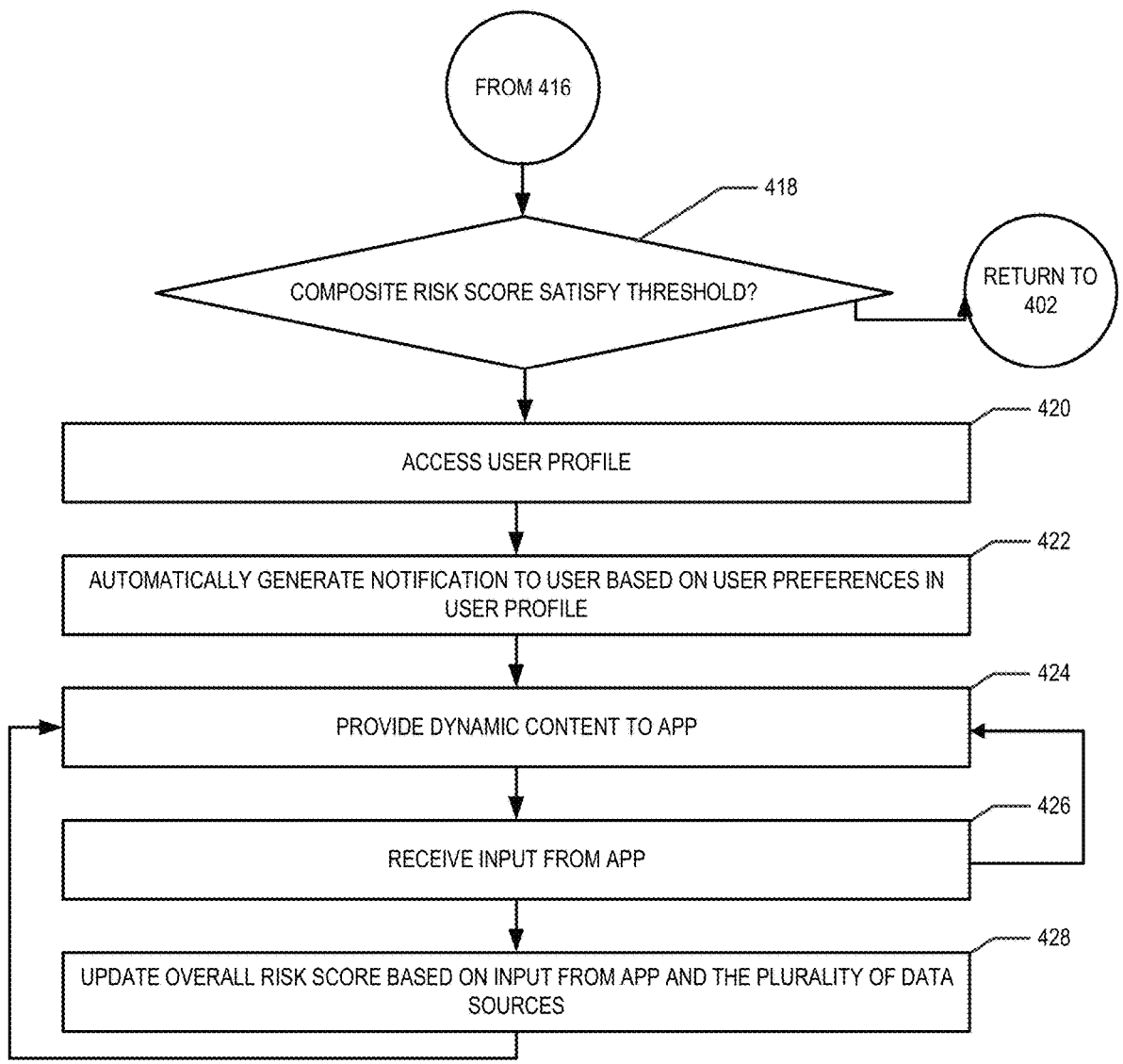

Reference will now be made to FIGS. 4A, 4B, 5A, 5B, and 6-10. FIGS. 4A and 4B are flowcharts for exemplary connections, operations, steps, and processes. FIGS. 5A and 5B illustrate exemplary features for ingestion by one or more machine learning models. FIG. 6 illustrates an exemplary dynamic content library. And FIGS. 7-10 provide exemplary interfaces that can be dynamically updated.

a. Brief Overview

1. Technical Problem

As previously noted, patients with chronic conditions are often under diagnosed for malnourishment (under nourished, over nourished, and not having proper nutrients in their system to fight particular conditions, illnesses, and/or diseases). Because diet and nutrition plays an important role in chronic disease management and one's overall health, personalized intervention is an important aspect for curbing disease-related malnourishment. And while technological solutions like fitness apps, fitness trackers, and/or the like allow consumers to track their dietary intake, plan menus, they do not offer dynamic personalization that's applicable for a patient's clinical condition. Through applied effort, ingenuity, and innovation, the inventors have developed methods, apparatus, systems, computing devices, computing entities, and/or for overcoming these challenges.

2. Technical Solution

Embodiments of the present invention provide a technological approach for using machine learning to score users within a micropopulation to predict the risk of malnourishment by leveraging statistical modeling methods, for example. In one embodiment, the machine learning implements an ensemble of learners trained to generate/predict the eventual probability of malnutrition for a patient (e.g., a composite risk score). An advantage of using ensembling is that bias is reduced while still keeping the variance low. Also, the variances (and errors) produced due to random initialization of complex black-box models like neural networks (and the ensuing gradient descent training) are averaged out due to ensembling and thus produce more reliable composite risk scores. And ensembling may yield better results when there is a significant diversity among the machine learning models (e.g., micropopulation machine learning models). This allows for significant differences among the micropopulation machine learning models with their outputs that ultimately being combined. Once generated, the composite risk scores can also be used to rank order patients from high-risk to low-risk.

Further, using the composite risk scores, the data analytic system 100 can automatically initiate one or more interventions (e.g., automatically generating a notification to download a health-related app) and provide dynamic content to a health-related app 800 based on the same. The dynamic content may include library content associated with a particular condition or composite risk score, dietary and exercise recommendations associated with a particular condition or composite risk score, and/or the like. The health-related app 800 may also provide real-time tracking of user biometric information/data, real-time user feedback, and/or the like.

Thus, the disclosed approach not only generates/predicts at-risk patients, but provides a digital solution that allows patients connect with a trusted specialist, who will ensure food and medical adherence are accomplished. The technical solution in this disclosure empowers patients to take the action and own their recovery path, instead of care providers having to persuade them and deal with resistance.

b. User Profiles

In one embodiment, to help accomplish the technical solution, a user (e.g., member, patient) may operate a user computing entity 30 to register/enroll for an account, subscription, program, and/or similar words used herein interchangeably. In one embodiment, a user (e.g., a user operating a user computing entity 30) may access a webpage, mobile application, application, dashboard, browser, interface, or portal to register. In another embodiment, the user may be automatically enrolled/registered for the same.

As part of the manual enrollment/registration process, a user (e.g., a user operating a user computing entity 30) may be requested to provide information/data (e.g., including user information/data, biographic information/data, biometric information/data, geographic information/data, entity information/data, payment information/data, and/or the like). The information/data may be manually input by a user, automatically provided by allowing access to other accounts, and/or using other techniques and approaches. Such information may be used to generate a user profile. The user profile may be associated with a username and/or an internal user identifier in association with the user profile, such as a global unique identifier (GUID), a universally unique identifier (UUID), and/or the like. For instance, in one embodiment, the user identifier may be a 128-bit value displayable as hexadecimal digits with groups separated by hyphens. In one embodiment, a user identifier may be used to uniquely identify a user profile.

As will be recognized, a user profile may comprise user information/data, such as a user identifier configured to uniquely identify the user (e.g., provider identifier, member identifier, and/or the like), a username, user contact information/data (e.g., name, one or more electronic addresses such as emails, instant message usernames, social media user name, and/or the like), user preferences (notification/message preferences), dietary preferences, generic vs. name brand preferences, privacy preferences, allergies, user account information/data, user credentials, information/data identifying one or more user computing entities 30 corresponding to the user, and/or the like.

The user profile may include one or more communication formats for communicating with the user as part of his or her notification/message preferences. The communication formats may include text notifications/messages (e.g., SMS, MMS), email notifications/messages, voice notifications/messages, video notifications/messages, picture notifications/messages (e.g., Instagram), social media notifications/messages (e.g., private social media created internally for entities, business social media (e.g., Yammer, SocialCast), or public social media (e.g., Facebook, Instagram, Twitter), and/or a variety of other notifications/messages in various communication formats. In addition to the one or more communication formats, the user (e.g., operating a user computing entity 30) can provide the corresponding electronic destination addresses to be used in providing information/data associated with the notification/message services to the user (e.g., email addresses, online handles, phone numbers, usernames, and/or the like). For instance, for text notifications/messages, the user may provide one or more cellular phone numbers. For email notifications/messages, the user may provide one or more email addresses (to receive emails or notifications through specific accounts). And for voice notifications/messages, the user may provide one or more phone numbers or other electronic destination addresses to which audio files can be delivered.

With the user profile, the data analytic system 100 may provide the user with various types of information/data regarding his or her health. As is described in greater detail, the user profile may also be used to provide the user with customized notifications and dynamic content customized for the user.

c. Health-Related Information/Data and Feature Processing

As indicated in step/operation 402 of process 400 of FIG. 4A, health-related information/data is received from various data sources 68A-68N. For example, the data analytic system 100 may connect with a variety of data sources 68A-68N to obtain transaction information/data, member information/data, provider information/data, clinical information/data, nutritional information/data, medication information/data, and other information/data.

As noted, the health-related information/data may comprise provider information/data having identifying information/data indicative of various providers. The provider information/data may comprise provider identifiers, provider locations, and/or the like. The health-related information/data may further comprise member information/data. The member information/data may comprise information/data for a member, such as age, gender, poverty rates, known health conditions, home location, profession, access to medical care, medical history, claim history, member ID, and/or the like. The health-related information/data may also comprise transaction information/data, such as claim information/data indicative of claims filed on behalf of a provider for services or products. Moreover, the claim information/data may further comprise prescription claim information/data. Prescription claim information/data may be used to extract information/data such as the identity of entities that prescribe certain drugs and the pharmacies that fill such prescriptions. The health-related information/data may also comprise clinical information/data, nutritional information/data, medication information/data, and other information/data. Thus, the health-related information/data may be from multiple dimensions—including food habits, (ir)regular food intake, clinical journeys and any clinical incidents (e.g., like weekly appointments, readmissions, medications), allergies, provider visits, medical codes, and/or the like.

Once received, the data analytic system 100 may perform processing on the health-related information/data to make the health-related information/data more suitable for analysis. Such processing may include cleansing the health-related information/data, normalizing the health-related information/data, predicting values for missing health-related information/data, and/or the like (step/operation 404 of FIG. 4B). As will be recognized, a variety of other approaches and techniques can be used to adapt to various needs and circumstances in making the health-related information/data more suitable for analysis.

In one embodiment, the health-related information may be further curated into information/data for specific micropopulations. A micropopulation may correspond to a specific condition, illness, and/or disease. For example, each of the following conditions, illnesses, and/or diseases may be used for cohorted groups people: dementia, depression, chronic obstructive pulmonary disease (COPD), stroke, musculoskeletal disorders, coronary heart failure (CHF), colon cancer, breast cancer, juvenile diabetes, chronic kidney disease (CDK), asthma, and/or the like.

For each micropopulation, the health-related information/data may be further curated using iterative feature engineering using manual, semi-automated, or automated techniques (step/operation 406 of FIG. 4B). For example, in one embodiment, a user with clinical expertise may curate the health-related information to engineer features for each micropopulation. In another embodiment, neural networks may be used for automated feature engineering for each micropopulation. The manually, semi-automatically, or automatically engineered features may be grouped into a various categories as shown in FIGS. 5A, 5B, and 5C. FIGS. 5A, 5B, and 5C represent at least portions of feature sets that can identified or extracted from the health-related information/data.

FIG. 5A shows exemplary member features (e.g., information/data associated with a particular member). As shown in this figure, member features can include, but are not limited to, age, gender, poverty rates, known health conditions, home location, profession, access to medical care, medical history, claim history, member ID, and/or the like.

FIG. 5B shows exemplary claim features (e.g., information/data associated with a particular claim). As shown in this figure, claim features may also include one or more diagnostic codes, treatment codes, treatment modifier codes, and/or the like. Such codes may be any code, such as Current Procedural Terminology (CPT) codes, billing codes, Healthcare Common Procedure Coding System (HCPCS) codes, ICD-10-CM Medical Diagnosis Codes, and/or the like. By way of example of billing codes, a patient may visit a provider because of discomfort in his lower leg. During the visit, the provider may examine the patient's lower leg and take an x-ray of the lower leg as part of an examination. The claim for the visit may have two distinct billing codes: billing code 99213 and billing code 73590. Billing code 99213 may be used to request payment/reimbursement for the visit, examination, and evaluation of the patient. Billing code 73590 may be used to request payment/reimbursement for the x-ray of the leg. Using such codes and code sets, various correlations can be determined as they related to recoverability.

FIG. 5C shows exemplary provider features (e.g., information/data associated with a particular provider). As shown in this figure, provider features may include, but are not limited to, demographics (e.g., the location in which the provider operations), contracted status, specialty, and/or one the like.

As previously noted, features may be engineered manually, semi-automatically, or automatically to produce feature sets. A feature set comprises one or more features. A feature set may comprise any features determined relevant to the corresponding micropopulation. Additional features may be grouped into demographic, socio-economic, preference, nutritional, clinical, operational, and/or service features.

In one embodiment, due to the temporal nature of some features, the data analytic system 100 may use a rolling window to accumulate features. By way of example, claim features or clinical features may be accumulated using a look-back over a rolling window of events (e.g., the past 6 months). The data analytic system 100 may also generate summarized feature information, treatment indicators, comorbidities, flags for exceptions or outliers, and/or the like.

d. Generating Risk Scores

As previously indicated, embodiments of the present invention use one or more machine learning models to generate/predict a micropopulation score for each micropopulation and use the micropopulation scores to generate/predict composite risk scores for users.

As will be recognized, training one or more machine learning algorithms to generate one or more machine learning models involves providing one or more training datasets to the machine learning algorithms (e.g., using the engineered feature sets with corresponding scoring). The training datasets contain the target outputs or variables that the machine-learning models are to eventually predict. The machine-learning algorithms detect patterns in the training datasets that map the input information/data attributes from the feature sets to the target outputs or variables and capture these patterns. The resulting machine-learning models are then able to generate predictions for new or unseen information/data for which the targets are unknown. The models are then validated using validation datasets.

As a result of the training, one or more machine learning models for each micropopulation are generated to generate/predict micropopulation scores for users (steps/operations 408, 410 of FIG. 4A). For instance, in one embodiment, the machine learning models comprise an ensemble of micropopulation learning models 69A-69N—with each micropopulation learning model 69A-69N trained to generate/predict a user's risk within the respective micropopulation. For example, there may be one or more micropopulation learning models 69A-69N for each micropopulation: one or more machine learning models that generate/predict a user's risk for dementia, one or more machine learning models that generate/predict a user's risk for depression, one or more machine learning models that generate/predict a user's risk for COPD, one or more machine learning models that generate/predict a user's risk for strokes, one or more machine learning models that generate/predict a user's risk for musculoskeletal disorders, one or more machine learning models that generate/predict a user's risk for CHF, one or more machine learning models that generate/predict a user's risk for colon cancer, one or more machine learning models that generate/predict a user's risk for breast cancer, one or more machine learning models that generate/predict a user's risk for juvenile diabetes, one or more machine learning models that generate/predict a user's risk for CDK, one or more machine learning models that generate/predict a user's risk for asthma, and/or the like. In other words, each micropopulation learning model 69A-69N is trained to generate/predict a risk score in its corresponding area. Table 1 provides exemplary micropopulation risk scores for a user in the domain [0,100] for some of the referenced micropopulations.

TABLE 1

Dementia: 025
Depression: 037
COPD: 069
Stroke: 074
. . .
Asthma: 085

These micropopulation risk scores represent the predicted likelihood that the user is at risk for the corresponding condition, illness, and/or disease. In addition to outputting the predicted micropopulation risk scores, the micropopulation learning model 69A-69N can also output the attributes associated with the micropopulation risk scores. In one embodiment, the attributes are features of the feature sets that are driving or underlying the risk scores.

As will be recognized, with the engineered feature sets used to train machine learning models 69A-69N, the micropopulation machine learning models 69A-69N are sufficiently independent such that they are not biased in the same direction. Moreover, the number of machine learning models for each micropopulation may be dependent upon the available information/data, the training time, and/or the accuracy desired. Additionally, the artificial intelligence engine 67 (e.g., executing on the analytic computing entity 65) may utilize a variety of linear and/or non-linear models as a part of the ensemble with the hyper parameters being further tuned as more information/data is obtained and the results from are verified. As previously noted, an advantage of using ensembling is that bias is reduced while still keeping the variance low. Also, the variances (and errors) produced due to random initialization of complex black-box models like neural networks (and the ensuing gradient descent training) are averaged out due to ensembling and thus producing more reliable composite risk score. And ensembling may yield better results when there is a significant diversity among the machine learning models (e.g., micropopulation machine learning models). This allows for significant differences among the micropopulation machine learning models with their outputs that are ultimately combined.

Accordingly, with at least two micropopulation risk scores generated/predicted for a user, the risk scores (and in some cases features) are ingested into a combining layer 70 (and/or composite machine learning model 71) of the artificial intelligence engine 67. The combining layer 70 (and/or composite machine learning model 71) uses the various outputs from the micropopulation machine learning models 69A-69N and applies one or more techniques, such as stacking, blending, or boosting (step/operation 412 of FIG. 4A). The combining layer 70 (and/or composite machine learning model 71) generates a composite risk score for the user (steps/operations 414, 416 of FIG. 4A). The composite risk score is indicative of the user's nutritional health. In one embodiment, the composite risk score is in the domain [1,100] and is output with associated attributes (e.g., features from feature sets) driving or underlying the composite risk score. This ensembled approach allows for comparison across micropopulations (e.g., cohorts of people with dementia compared to cohorts of people depression). Table 2 provides exemplary composite risk scores for a user in the domain [0,100] for some of the referenced micropopulations.

TABLE 2

Jane Doe's Composite Risk Score: 53
Risk Score Attributes: Depression: PMDD e. Automatically Initiating Actions In one embodiment, one or more configurable thresholds can be used to automatically initiate specific actions based at least in part on a user's composite risk score, associated attributes, and/or user profile. The specific actions may include generating, queueing and transmitting one or more automated notifications/messages to the user; initiating one or more interventions; electronically flagging medical records for monitoring or review; generating, queueing and transmitting one or more automated notifications/messages to the user's provider; and/or the like. In one embodiment, the one or more configurable thresholds may correspond to all composite risk scores. In another embodiment, the one or more configurable thresholds may correspond to the specific associated attributes of the composite risk scores. For example, a first configurable threshold may correspond to all composite risk scores that are output with the associated attribute of dementia, such as configurable threshold 80. As another example, a second configurable threshold may correspond to all composite risk scores that are output with the associated attribute of depression, such as configurable threshold 64. As will be recognized, a variety of other approaches and techniques can be used to adapt to various needs and circumstances.

Figure 7:
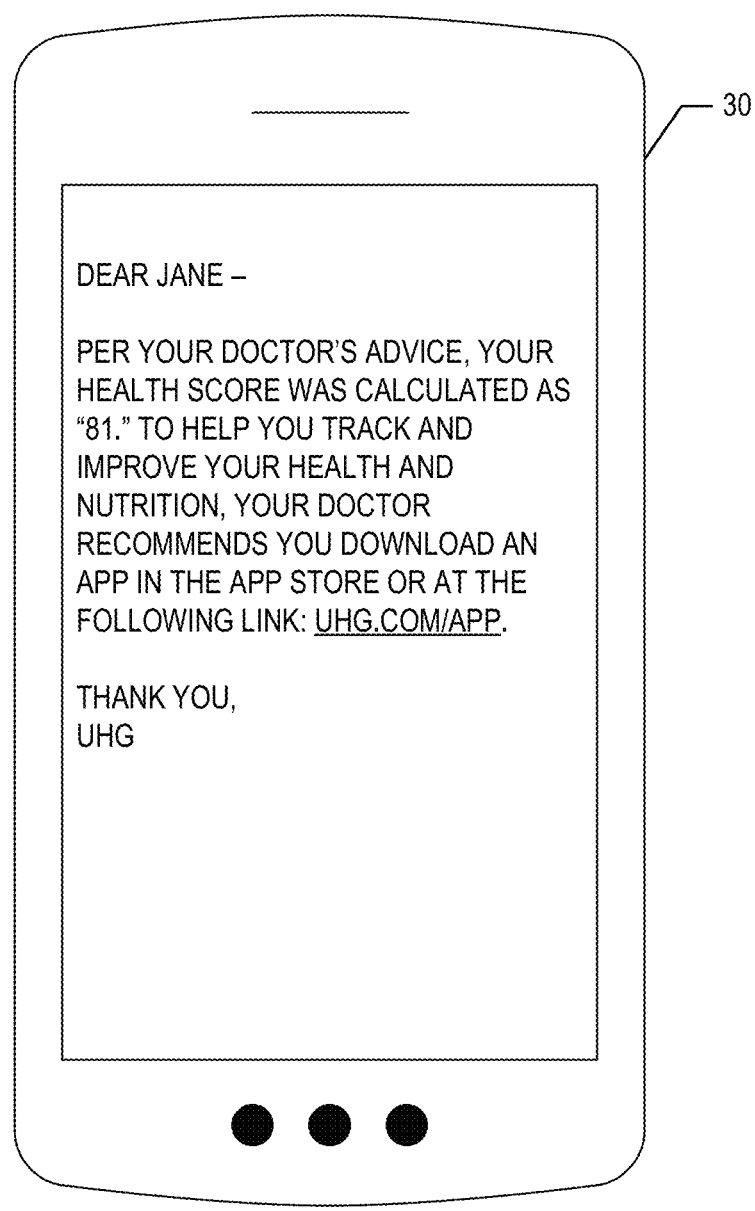
Figure 8:
Figure 9:
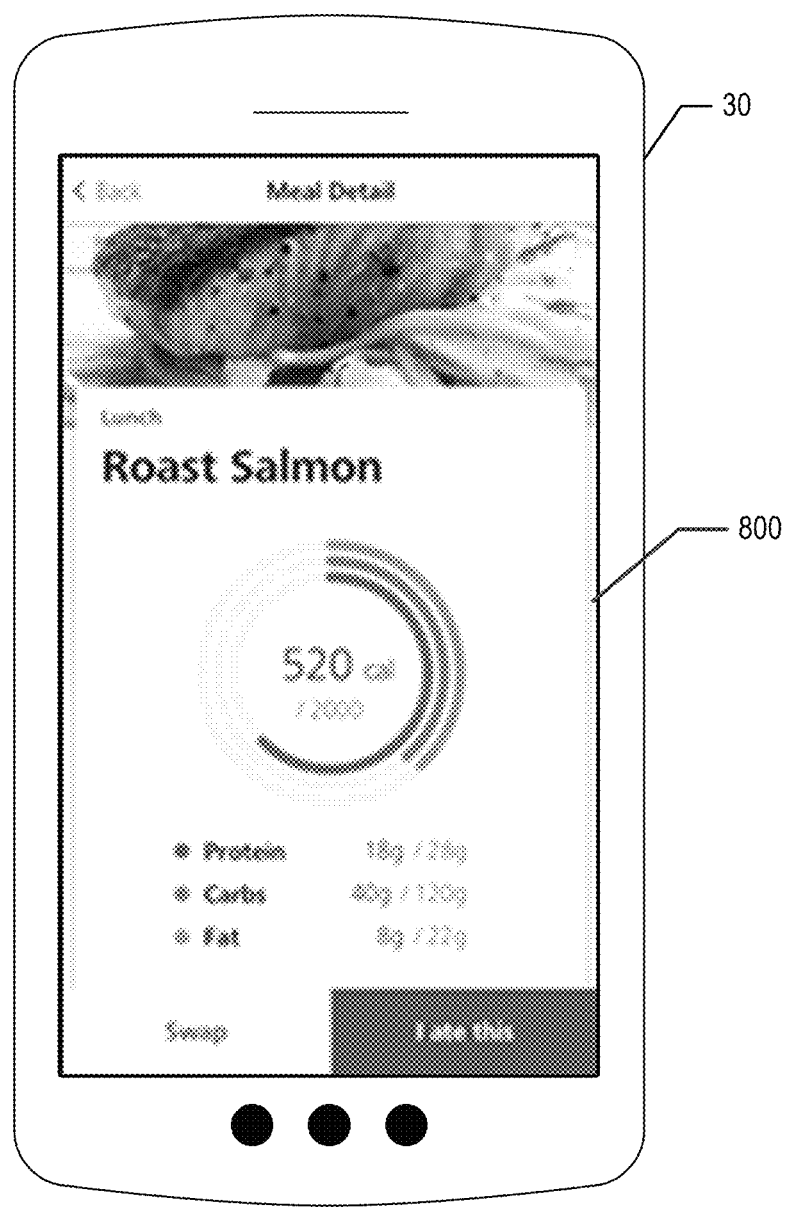
Figure 10:
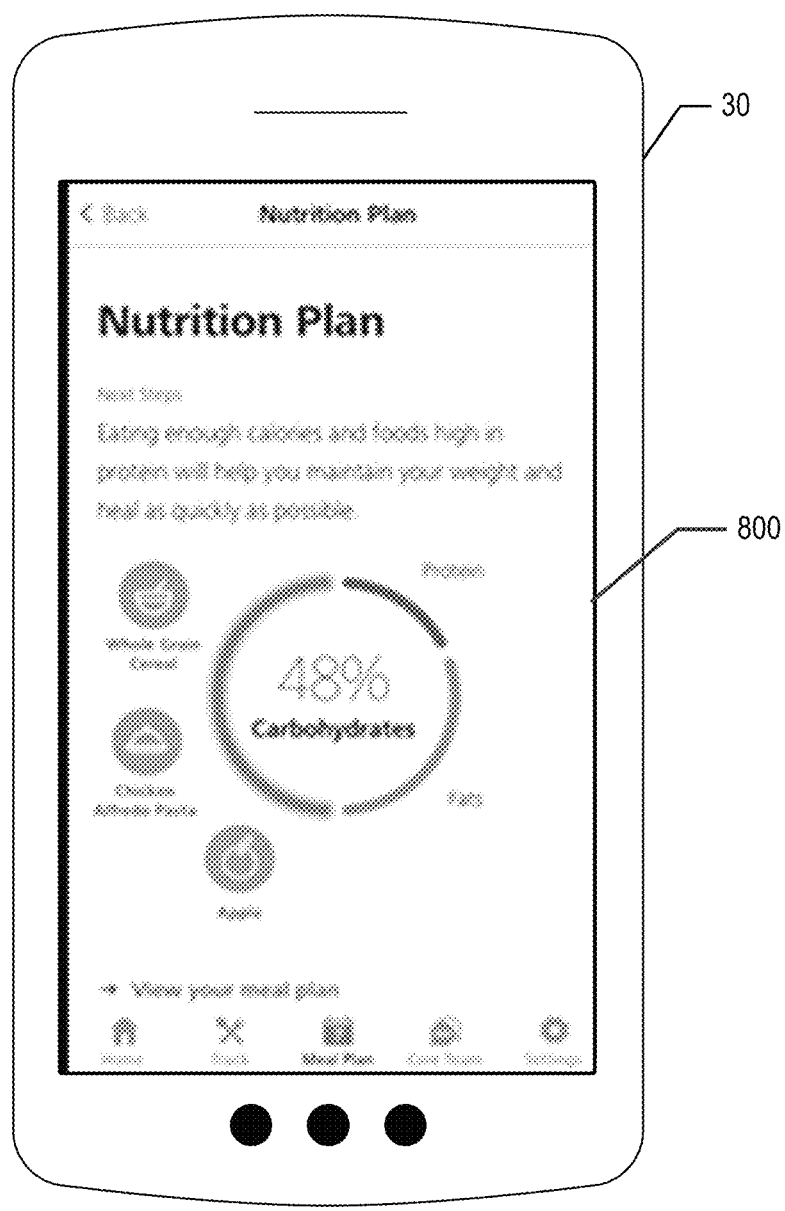

In a particular embodiment, a composite risk score satisfying one or more configurable thresholds may automatically initiate a message or notification to the corresponding user based at least in part on a user's composite risk score, associated attributes, and/or user profile. For example, if Jane Doe's composite risk score were 81 and that score satisfied either a general composite threshold, a specific depression threshold, and/or the like, the data analytic system 100 may access the user's profile and generate, queue, and transmit a notification/message to the user based on his/her user preferences—such as an SMS message, email message, MMS message, and/or the like. In one embodiment, as shown in FIG. 7, the notification/message may comprise a uniform resource identifier (URI) (e.g., a link) or other information about where a health-related app 800 can be downloaded. As described below, the health-related app 800 may provide real-time feedback and/or recommendations to the user to influence him/her and improve his/her health. In another embodiment, the notification/message may simply comprise a configuration that enables the user computing entity 30 (e.g., smartphone, wearables, or other associated devices) to interact with the data analytic system 100 using its native functions.

f. Providing Dynamic Content to User Interface

In one embodiment, once the user downloads the health-related app 800 on his/her user computing entity 30, the data analytic system 100 can provide the health-related app 800 with a dynamic content for the user (step/operation 424, 426 of FIG. 4B). In one embodiment, the dynamic content may be from a dynamic content library 600. For example, the dynamic content library 600 may include information about diagnoses, symptoms, treatments, causes, and risk and preventions for various conditions, illnesses, and/or diseases. As shown in FIG. 6, the information in the dynamic content library 600 corresponds to the micropopulations. Thus, if the associated attributes of the user's composite risk score include depression or PMDD, the data analytic system 100 may provide the content for depression and/or PMDD to the health-related app 800 for the user. This may include transmitting the dynamic library content to the health-related app 800, unlocking access to the dynamic content in the health-related app 800, and/or the like. As will be recognized, this provides the user with access to health-related information for illnesses, conditions, and/or diseases of the user.

In one embodiment, the health-related app 800 can collect real time information/data from the user to provide better recommendations and/or update the micropopulation risk scores and/or the composite risk score. The real-time information/data collected may include biometric information/data, dietary intake information/data, environmental information/data, image information/data, sleep information/data, purchase information/data, location information/data, and/or any other types of information/data. With the real-time information/data, the health-related app 800 can track a user's day-to-day activities, track the user's food intake, provide additional dynamic content, and/or the like (step/operation 424, 426 of FIG. 4B).

By way of example, a user in the breast cancer micropopulation initially assigned a composite risk score of 80 (with the associate attribute of breast cancer) is provided an SMS text with a link to the health-related app 800. The user then registers with the health-related app 800 and includes his/her additional preferences (e.g., vegan, allergic to broccoli), which were not pre populated—see FIG. 8. Using this additional information, the health-related app 800 can provide the user with meal recommendations that avoid broccoli and meats, for example—see FIG. 9.

In another example, a user fighting colorectal cancer is initially assigned a composite risk score of 65 (with the associate attribute of colon cancer), which triggered an email to the user with information recommending that the user download the health-related app 800. The, when the user swaps a recommended toast with nut butter breakfast with bacon and ham causing a protein deficiency (which is input via the health-related app 800 and provided to the data analytic system 100), the data analytic system 100 adjusts the composite risk score (if necessary) and adjusts the next recommendations (for display via the health-related app 800) to contain protein rich foods, such as lentil soup.

One of the advantages of this technological solution is early detection of conditions, illnesses, and/or diseases and real-time intervention strategies. These iterative steps/operations (e.g., steps/operations 424, 426, 428) provide the user with the most accurate and relevant content to the user. As will be recognized, a variety of other approaches and techniques can be used to adapt to various needs and circumstances.

g. Updating Scores

In one embodiment, the data analytic system 100 continuously retrains the models to adapt to changes in features, member features, provider features, recovery features, and/or the like. As a result, the predicted risk scores determined by the one or more machine learning models become stale. Thus, the data analytic system 100 continuously retrains the machine learning models by rapidly generating the new feature sets and generating/predicting updated risk scores (e.g., steps/operations 424, 426, 428 of FIG. 4B).

As will be recognized, the retraining may be initiated in a variety of ways. In one embodiment, the data analytic system 100 can retrain the one or more machine learning models on a fixed schedule (e.g., hourly, daily, weekly, and/or the like). In another embodiment, the data analytic system 100 can retrain the one or more machine learning models based at least in part on one or more automated triggers. For example, the data analytic system 100 may execute change detection algorithms to detect changes in claim features, provider features, member features, and/or other relevant features. Examples of such changes may be the discontinued use of particular codes, use of new codes, changes in recovery rates for providers, changes in recovery rates for types of claims, changes in particular distributions, new locations being services, types of plans being accepted, and/or the like.

IV. CONCLUSION

Many modifications and other embodiments of the inventions set forth herein will come to mind to one skilled in the art to which these inventions pertain having the benefit of the teachings presented in the foregoing descriptions and the associated drawings. Therefore, it is to be understood that the inventions are not to be limited to the specific embodiments disclosed and that modifications and other embodiments are intended to be included within the scope of the appended claims. Although specific terms are employed herein, they are used in a generic and descriptive sense only and not for purposes of limitation.

The invention claimed is:

1. A computer-implemented method comprising:
    training, by one or more processors, a plurality of micropopulation machine learning models using machine learning, wherein the plurality of micropopulation machine learning models comprise one or more first micropopulation machine learning models and one or more second micropopulation machine learning models, and wherein each micropopulation machine learning model of the plurality of micropopulation machine learning models is independently initialized and independently trained;
    receiving, by the one or more processors, health-related data associated with a user;
    generating, by the one or more processors, a first feature set comprising one or more first features from the health-related data as input for the one or more first micropopulation machine learning models, wherein the one or more first micropopulation machine learning models generate predictions for at least one of a first condition, a first illness, or a first disease;
    generating, by the one or more processors, a second feature set comprising one or more second features from the health-related data as input for the one or more second micropopulation machine learning models, wherein the one or more second micropopulation machine learning models generate predictions for at least one of a second condition, a second illness, or a second disease;
    providing, by the one or more processors, the first feature set as input to the one or more first micropopulation machine learning models of the artificial intelligence engine;
    generating, by the one or more processors and using the one or more first micropopulation machine learning models of the artificial intelligence engine, a first predicted micropopulation risk score for the user, wherein the first micropopulation risk score indicates a likelihood that the user is at risk for the first condition, the first illness, or the first disease;
    providing, by the one or more processors, the second feature set as input to the one or more second micropopulation machine learning models of the artificial intelligence engine;
    generating, by the one or more processors and using the one or more second micropopulation machine learning models of the artificial intelligence engine, a second predicted micropopulation risk score for the user, wherein the second micropopulation risk score indicates a likelihood that the user is at risk for the second condition, the second illness, or the second disease;
    providing, by the one or more processors, the first predicted risk score and the second predicted risk score to a combining layer of the artificial intelligence engine, wherein the combining layer comprises a composite machine learning model trained using machine learning;
    generating, by the one or more processors and using the combining layer of the artificial intelligence engine, a predicted composite risk score for the user based at least in part on the first micropopulation risk score and the second micropopulation risk score;
    determining whether the predicted composite risk score for the user satisfies a composite risk score threshold; and
    responsive to determining that the predicted composite risk score for the user satisfies the composite risk score threshold:
    accessing a user profile for the user,
    automatically providing a notification to the user based at least in part on the user's notifications preferences stored in the user profile, wherein the notification comprises a uniform resource identifier (URI) from which a mobile app can be accessed to download, and
    responsive to the user downloading the mobile app, providing access to a dynamic content library associated with at least one of a first feature associated with the first predicted micropopulation risk score, a second feature associated with the second predicted micropopulation risk score, or a composite risk score feature associated with the predicted composite risk score.

2. The computer-implemented method of claim 1, wherein a user computing entity is executing the mobile app and the method further comprises:
    identifying the composite risk score feature associated with the predicted composite risk score; and
    providing first dynamic content to the mobile app corresponding to the composite risk score feature associated with the predicted composite risk score.

3. The computer-implemented method of claim 2 further comprising:
    receiving real-time data from the mobile app; and
    responsive to receiving the real-time data from the mobile app, providing second dynamic content to the mobile app based at least in part on the real-time data.

4. The computer-implemented method of claim 1, wherein the one or more first micropopulation machine learning models, the one or more second micropopulation machine learning models, and the composite machine learning model are part of an ensemble machine learning platform.

5. A computer program product comprising a non-transitory computer readable medium having computer program instructions stored therein, the computer program instructions when executed by a processor, cause the processor to:
- train a plurality of micropopulation machine learning models using machine learning, wherein the plurality of micropopulation machine learning models comprise one or more first micropopulation machine learning models and one or more second micropopulation machine learning models, and wherein each micropopulation machine learning model of the plurality of micropopulation machine learning models is independently initialized and independently trained;
- receive health-related data associated with a user;
- generate a first feature set comprising one or more first features from the health-related data as input for the one or more first micropopulation machine learning models, wherein the one or more first micropopulation machine learning models generate predictions for at least one of a first condition, a first illness, or a first disease;
- generate a second feature set comprising one or more second features from the health-related data as input for the one or more second micropopulation machine learning models, wherein the one or more second micropopulation machine learning models generate predictions for at least one of a second condition, a second illness, or a second disease;
- provide the first feature set as input to the one or more first micropopulation machine learning models of the artificial intelligence engine;
- generate, using the one or more first micropopulation machine learning models of the artificial intelligence engine, a first predicted micropopulation risk score for the user, wherein the first micropopulation risk score indicates a likelihood that the user is at risk for the first condition, the first illness, or the first disease;
- provide the second feature set as input to the one or more second micropopulation machine learning models of the artificial intelligence engine;
- generate, using the one or more second micropopulation machine learning models of the artificial intelligence engine, a second predicted micropopulation risk score for the user, wherein the second micropopulation risk score indicates a likelihood that the user is at risk for the second condition, the second illness, or the second disease;
- provide the first predicted risk score and the second predicted risk score to a combining layer of the artificial intelligence engine, wherein the combining layer comprises a composite machine learning model trained using machine learning;
- generate, using the combining layer of the artificial intelligence engine, a predicted composite risk score for the user based at least in part on the first micropopulation risk score and the second micropopulation risk score;
- determine whether the predicted composite risk score for the user satisfies a composite risk score threshold; and
- responsive to determining that the predicted composite risk score for the user satisfies the composite risk score threshold:
  - access a user profile for the user,
  - automatically provide a notification to the user based at least in part on the user's notifications preferences stored in the user profile, wherein the notification comprises a uniform resource identifier (URI) from which a mobile app can be accessed to download, and
  - responsive to the user downloading the mobile app, provide access to a dynamic content library associated with at least one of a first feature associated with the first predicted micropopulation risk score, a second feature associated with the second predicted micropopulation risk score, or a composite risk score feature associated with the predicted composite risk score.

6. The computer program product of claim 5, wherein a user computing entity is executing the mobile app, and wherein the computer program instructions when executed by a processor, further cause the processor to:
- identify the composite risk score feature associated with the predicted composite risk score; and
- provide first dynamic content to the mobile app corresponding to the composite risk score feature associated with the predicted composite risk score.

7. The computer program product of claim 6, wherein the computer program instructions when executed by a processor, further cause the processor to:
- receive real-time data from the mobile app; and
- responsive to receiving the real-time data from the mobile app, provide second dynamic content to the mobile app based at least in part on the real-time data.

8. The computer program product of claim 5, wherein the one or more first micropopulation machine learning models, the one or more second micropopulation machine learning models, and the composite machine learning model are part of an ensemble machine learning platform.

9. A computing system comprising a non-transitory computer readable storage medium and one or more processors, the computing system configured to:
- train a plurality of micropopulation machine learning models using machine learning, wherein the plurality of micropopulation machine learning models comprise one or more first micropopulation machine learning models and one or more second micropopulation machine learning models, and wherein each micropopulation machine learning model of the plurality of micropopulation machine learning models is independently initialized and independently trained;
- receive health-related data associated with a user;
- generate a first feature set comprising one or more first features from the health-related data as input for the one or more first micropopulation machine learning models, wherein the one or more first micropopulation machine learning models generate predictions for at least one of a first condition, a first illness, or a first disease;
- generate a second feature set comprising one or more second features from the health-related data as input for the one or more second micropopulation machine learning models, wherein the one or more second micropopulation machine learning models generate predictions for at least one of a second condition, a second illness, or a second disease;
- provide the first feature set as input to the one or more first micropopulation machine learning models of the artificial intelligence engine;
- generate, using the one or more first micropopulation machine learning models of the artificial intelligence engine, a first predicted micropopulation risk score for the user, wherein the first micropopulation risk score indicates a likelihood that the user is at risk for the first condition, the first illness, or the first disease;
- provide the second feature set as input to the one or more second micropopulation machine learning models of the artificial intelligence engine;

generate, using the one or more second micropopulation machine learning models of the artificial intelligence engine, a second predicted micropopulation risk score for the user, wherein the second micropopulation risk score indicates a likelihood that the user is at risk for the second condition, the second illness, or the second disease;

provide the first predicted risk score and the second predicted risk score to a combining layer of the artificial intelligence engine, wherein the combining layer comprises a composite machine learning model trained using machine learning;

generate, using the combining layer of the artificial intelligence engine, a predicted composite risk score for the user based at least in part on the first micropopulation risk score and the second micropopulation risk score;

determine whether the predicted composite risk score for the user satisfies a composite risk score threshold; and responsive to determining that the predicted composite risk score for the user satisfies the composite risk score threshold:

access a user profile for the user, automatically provide a notification to the user based at least in part on the user's notifications preferences stored in the user profile, wherein the notification comprises a uniform resource identifier (URI) from which a mobile app can be accessed to download, and responsive to the user downloading the mobile app, provide access to a dynamic content library associated with at least one of a first feature associated with the first predicted micropopulation risk score, a second feature associated with the second predicted micropopulation risk score, or a composite risk score feature associated with the predicted composite risk score.

10. The computing system of claim 9, wherein the computing system is further configured to:

Identify the composite risk score feature associated with the predicted composite risk score; and provide first dynamic content to the mobile app corresponding to the composite risk score feature associated with the predicted composite risk score.

11. The computing system of claim 10, wherein the computing system is further configured to:

receive real-time data from the mobile app; and responsive to receiving the real-time data from the mobile app, provide second dynamic content to the mobile app based at least in part on the real-time data.

12. The computing system of claim 9, wherein the one or more first micropopulation machine learning models, the one or more second micropopulation machine learning models, and the composite machine learning model are part of an ensemble machine learning platform.

* * * * *